US009986948B2

(12) United States Patent
Sudo

(10) Patent No.: US 9,986,948 B2
(45) Date of Patent: Jun. 5, 2018

(54) ELECTRONIC DEVICE AND METHOD

(71) Applicant: KABUSHIKI KAISHA TOSHIBA, Minato-ku, Tokyo (JP)

(72) Inventor: Takashi Sudo, Fuchu Tokyo (JP)

(73) Assignee: KABUSHIKI KAISHA TOSHIBA, Tokyo (JP)

( * ) Notice: Subject to any disclaimer, the term of this patent is extended or adjusted under 35 U.S.C. 154(b) by 189 days.

(21) Appl. No.: 14/823,153

(22) Filed: Aug. 11, 2015

(65) Prior Publication Data

US 2015/0342524 A1 Dec. 3, 2015

Related U.S. Application Data

(63) Continuation of application No. PCT/JP2013/063417, filed on May 14, 2013.

(51) Int. Cl.

| | |
|---|---|
| ***G08C 19/22*** | (2006.01) |
| ***A61B 5/00*** | (2006.01) |
| ***G06F 21/62*** | (2013.01) |
| ***G06F 21/35*** | (2013.01) |
| ***H04L 29/06*** | (2006.01) |
| ***H04L 29/08*** | (2006.01) |
| *A61B 5/0402* | (2006.01) |

(Continued)

(52) U.S. Cl.

CPC ............ *A61B 5/6802* (2013.01); *G06F 21/35* (2013.01); *G06F 21/62* (2013.01); *G16H 10/60* (2018.01); *H04L 63/083* (2013.01); *H04L 67/10* (2013.01); *A61B 5/0015* (2013.01); *A61B 5/01* (2013.01); *A61B 5/02438* (2013.01); *A61B 5/0402* (2013.01); *A61B 2562/0219* (2013.01)

(58) Field of Classification Search

CPC . A61B 2562/0219; A61B 5/0015; A61B 5/01; A61B 5/02438; A61B 5/0402; A61B 5/6802; G06F 19/322; G06F 21/35; G06F 21/62

USPC ................................ 340/870.7, 870.8, 870.9

See application file for complete search history.

(56) References Cited

U.S. PATENT DOCUMENTS 6,757,719 B1 * 6/2004 Lightman ............ G06Q 20/383 455/419
7,009,511 B2 3/2006 Mazar et al.

(Continued)

FOREIGN PATENT DOCUMENTS

JP 2000-148860 A 5/2000
JP 2001-195368 A 7/2001

(Continued)

OTHER PUBLICATIONS

English Translation of International Preliminary Report on Patentability issued by The International Bureau of WIPO on Nov. 17, 2015 in the corresponding PCT Application No. PCT/JP2013/063417—6 pages.

(Continued)

*Primary Examiner* — Ojiako Nwugo

(74) *Attorney, Agent, or Firm* — Knobbe, Martens, Olson & Bear, LLP

(57) ABSTRACT

According to one embodiment, a wearable electronic device includes communication circuitry configured to communicate with an external device, and transmit access right information to the external device, the access right information for a write access right to first data stored in a server, the first data corresponding to a user of the electronic device.

17 Claims, 6 Drawing Sheets

Daily vital-sign cloud server 40
Daily vital-sign database 40A
Medical information cloud server 50
Medical information database 50A
60
Wearable vital sensor 10
Computer 30
Electronic medical record application 30A
Near-field communication terminal 20

(51) Int. Cl.

| | |
|---|---|
| *A61B 5/01* | (2006.01) |
| *A61B 5/024* | (2006.01) |

(56) References Cited

U.S. PATENT DOCUMENTS

| | | | | |
|---|---|---|---|---|
| 7,202,773 | B1 | 4/2007 | Oba et al. | |
| 9,094,383 | B2 | 7/2015 | Garcia Morchon et al. | |
| 9,184,458 | B2 | 11/2015 | Ishiguro et al. | |
| 2006/0106646 | A1 | 5/2006 | Squilla et al. | |
| 2007/0197878 | A1* | 8/2007 | Shklarski | A61B 5/02055 600/300 |
| 2008/0216171 | A1* | 9/2008 | Sano | H04L 9/32 726/19 |
| 2008/0294058 | A1* | 11/2008 | Shklarski | A61B 5/02055 600/502 |
| 2009/0105552 | A1 | 4/2009 | Nishiyama et al. | |
| 2010/0092812 | A1 | 4/2010 | Ishiguro et al. | |
| 2011/0022411 | A1 | 1/2011 | Hjelm et al. | |

FOREIGN PATENT DOCUMENTS

| | | | |
|---|---|---|---|
| JP | 2005-006824 | | 1/2005 |
| JP | 2005-301448 | | 10/2005 |
| JP | 2006-122610 | | 5/2006 |
| JP | 2008-043702 | | 2/2008 |
| JP | 2008-521130 | | 6/2008 |
| JP | 2008-186321 | | 8/2008 |
| JP | 2008-198028 | | 8/2008 |
| JP | 2008-276353 | | 11/2008 |
| JP | 2008-276959 | A | 11/2008 |
| JP | 2009-042804 | | 2/2009 |
| JP | 2009-095583 | | 5/2009 |
| JP | 2010-194334 | | 9/2010 |
| JP | 2011-521493 | | 7/2011 |
| JP | 2011-527464 | | 10/2011 |
| JP | 2013-030157 | | 2/2013 |
| JP | 2013-114289 | A | 6/2013 |

OTHER PUBLICATIONS

Office Action dated Jul. 19, 2016 of Japanese Patent Application 2015-516790—8 pages.

International Search Report for International Application No. PCT/JP2013/063417, dated Aug. 20, 2013, in 5 pages.

* cited by examiner

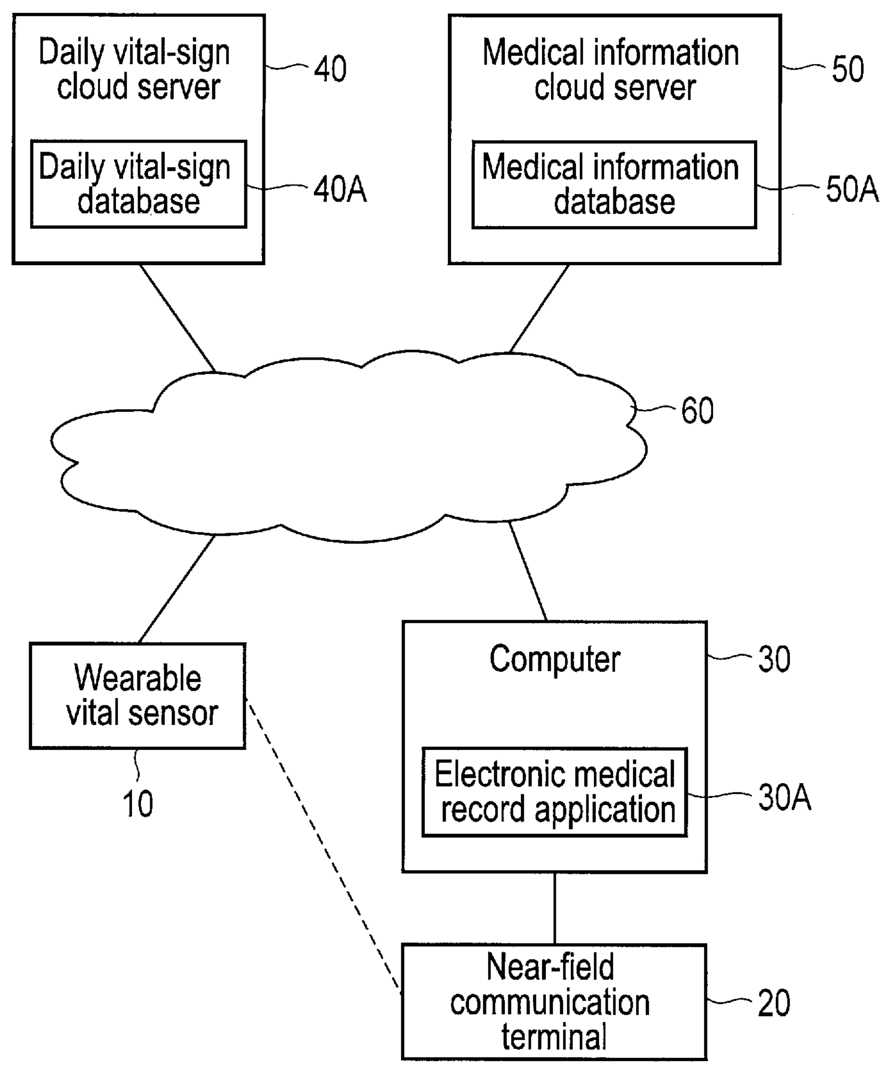
F I G. 1

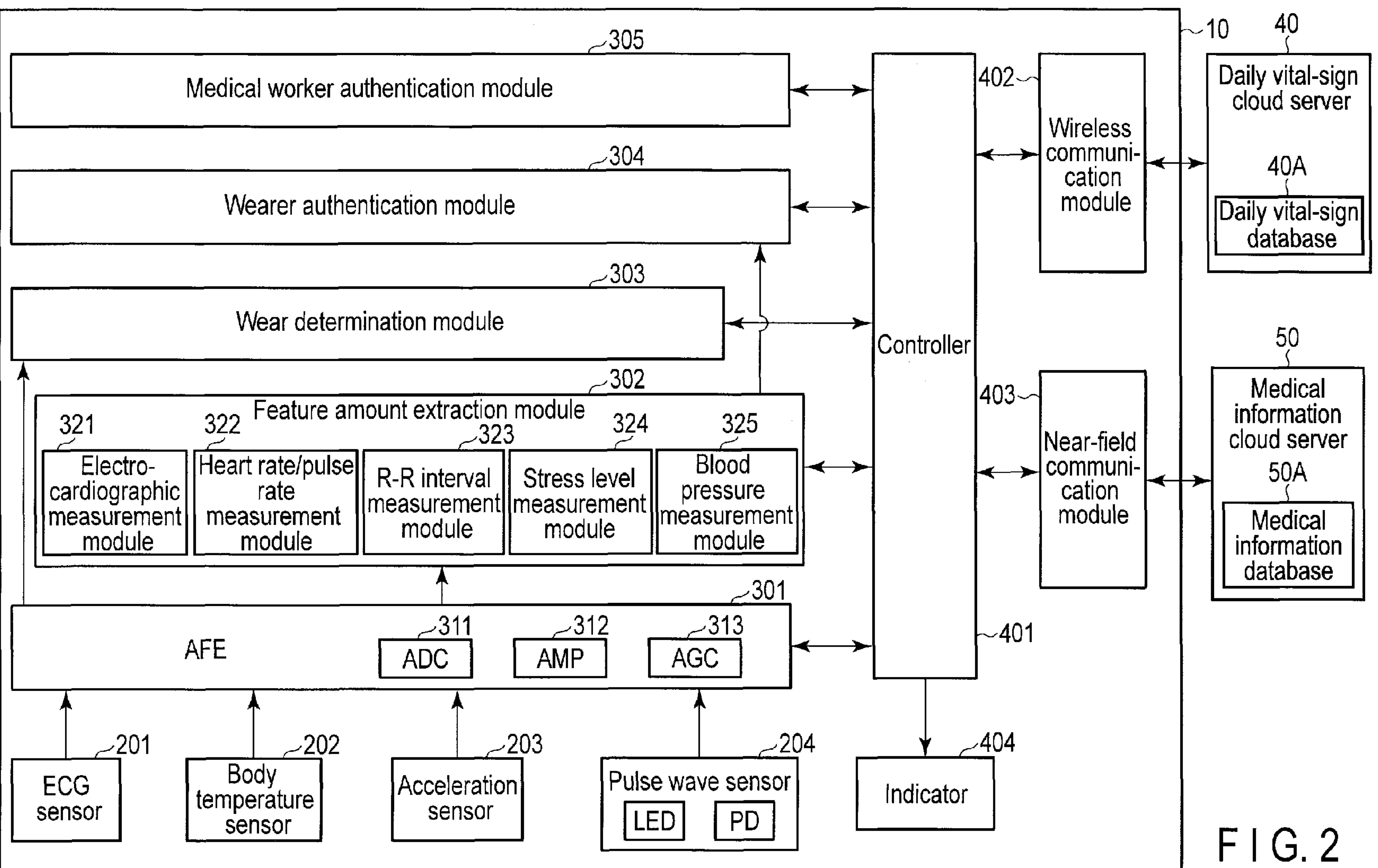
F I G. 2

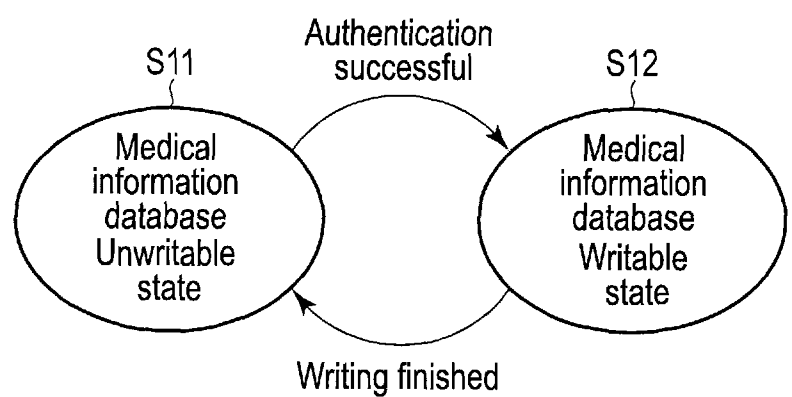
F I G. 5

ELECTRONIC DEVICE AND METHOD

CROSS-REFERENCE TO RELATED APPLICATIONS

This application is a Continuation Application of PCT Application No. PCT/JP2013/063417, filed May 14, 2013, the entire contents of which are incorporated herein by reference.

FIELD

Embodiments described herein relate generally to an electronic device and a method.

BACKGROUND

Recently, preventive medicine and healthcare in ordinary homes have attracted attention. Moreover, medical devices are being made smaller. Attachment of a compact device to the human body to measure vital signals such as the pulse wave is suggested.

When a user wearing a device has an examination in a medical institution, for example, a doctor writes medical information such as the diagnosis and prescribed drugs in a medical record. Recently, electronic medical records which are managed by computers have become widespread. Sharing of electronic medical records with medical institutions is suggested.

When electronic medical records are shared with medical institutions, it is desired not to write into the records when the person is not present in the institution.

BRIEF DESCRIPTION OF THE DRAWINGS

A general architecture that implements the various features of the embodiments will now be described with reference to the drawings. The drawings and the associated descriptions are provided to illustrate the embodiments and not to limit the scope of the invention.

FIG. 1 is a block diagram showing an example of a configuration of a healthcare service system according to an embodiment.

FIG. 2 is a block diagram showing an example of a configuration of an electronic device according to the embodiment.

FIG. 5 exemplarily shows the state transition of a medical information database when authentication is successful.

DETAILED DESCRIPTION

Figure 3:
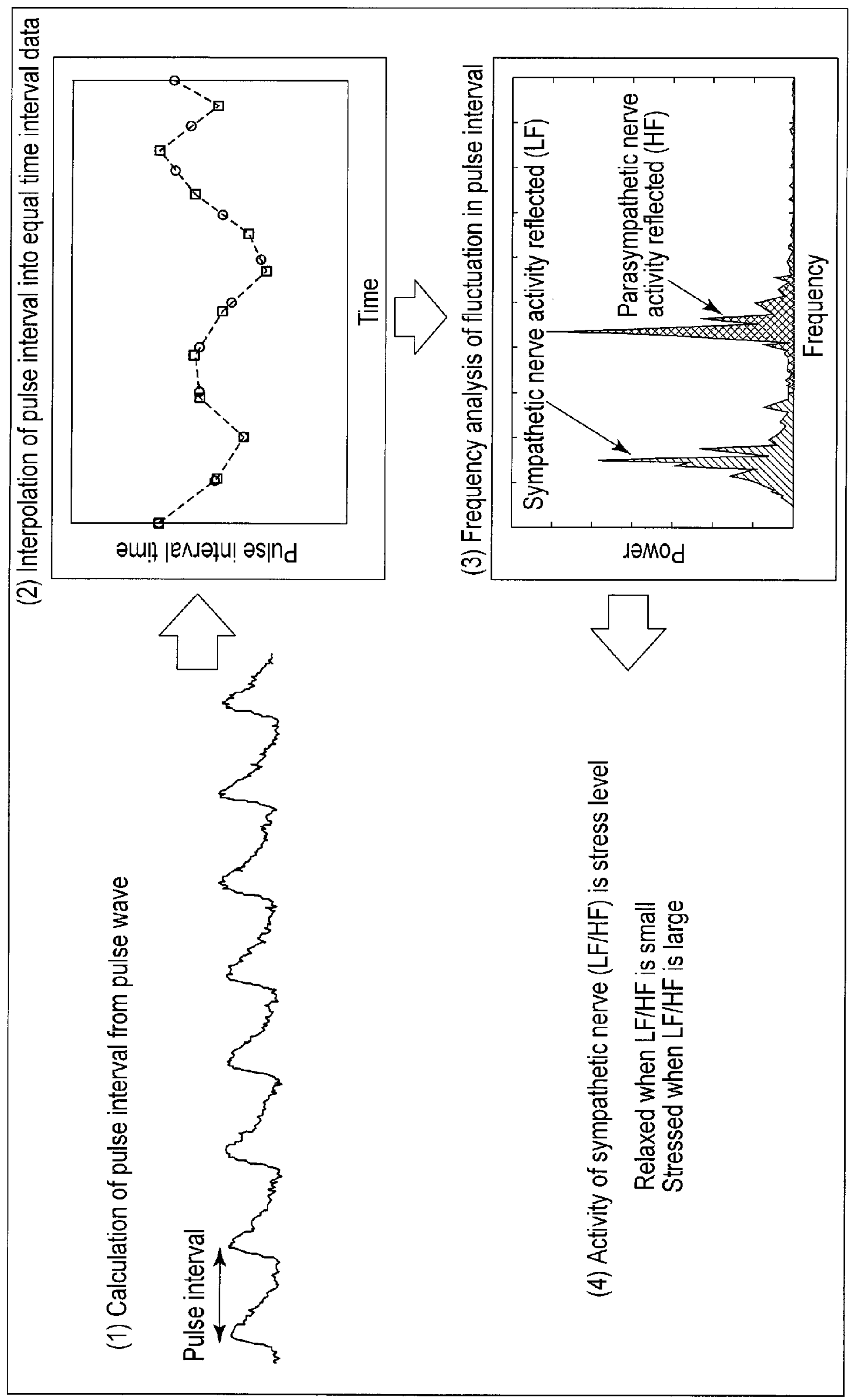
FIG. 3 exemplarily explains an operation for calculating the stress level (stress index).

Various embodiments will be described hereinafter with reference to the accompanying drawings.

In general, according to one embodiment, a wearable electronic device includes communication circuitry configured to communicate with an external device, and transmit access right information to the external device, the access right information for a write access right to first data stored in a server, the first data corresponding to a user of the electronic device.

FIG. 1 shows a configuration of a healthcare service system.

The healthcare service system includes, for example, a wearable vital sensor 10, a near-field communication terminal 20, a personal computer 30, a daily vital-sign cloud server 40 and a medical information cloud server 50. An electronic device may be realized as the wearable vital sensor 10.

The wearable vital sensor 10 measures plural vital signs such as the pulse wave, the electrocardiogram and the body motion. The wearable vital sensor 10 is incorporated into glasses, earphones, a watch, etc. The wearable vital sensor 10 authenticates whether or not the wearer is a valid person based on the measured vital signs. The daily vital signals are stored in a daily vital-sign database 40A corresponding to the authenticated person in the daily vital-sign cloud server 40 connected to a network 60.

A medical worker ID and a read access password are given to a medical worker who works in a hospital, a pharmacy, etc. The medical worker ID and the read access password are transmitted from the computer 30 to the daily vital-sign cloud server 40. When the authentication is successful, access to the daily vital-sign database 40A is permitted. At this time, the computer 30 is allowed to read the data in the daily vital-sign database 40A and is not allowed to change the data in the daily vital-sign database 40A.

The medical information cloud server 50 connected to the network 60 includes a medical information database 50A corresponding to the wearer. Information described in a medical record is recorded in the medical information database 50A. The information described in the medical record includes the inspection result, the diagnosis and prescribed drugs.

The medical worker ID and the read access password are transmitted from the computer 30 to the medical information cloud server 50. When the authentication is successful, access to the medical information database 50A is permitted. At this time, the computer 30 is allowed to read the data in the medical information database 50A and is not allowed to change the data in the medical information database 50A.

The near-field communication terminal 20 has the shape of a flat plate. When the wearable vital sensor 10 is placed on the near-field communication terminal 20, communication is performed between the computer 30 and the wearable vital sensor 10.

When the wearer goes to a medical institution such as a hospital or a pharmacy, the wearer removes the wearable vital sensor 10. The removed wearable vital sensor 10 is placed on the near-field communication terminal 20. An authentication process is performed between the wearable vital sensor 10 and an electronic medical record application 30A executed by the computer 30. This authentication (medical authentication) is performed to confirm whether or not the operator of the computer 30 is a true worker in a medical institution. When the medical authentication is successful, a user ID showing the wearer of the wearable vital sensor 10 and a write access password are informed from the wearable vital sensor 10 to the electronic medical record application 30A as access right information to provide the computer 30 with a write access right to the medical information database 50A. The user ID and the write access password are transmitted from the electronic medical record application 30A to the medical information cloud server 50. When the authentication performed by the medical information cloud server 50 is successful, data input in the medical information database 50A in the medical information cloud server 50 is permitted.

The electronic medical record application 30A reads vital signs from the daily vital-sign database 40A and generates data for displaying tables or graphs based on the read vital signs. The electronic medical record application 30A reads medical information from the medical information database 50A. The electronic medical record application 30A performs a process for displaying a medical record, etc., based on the read electronic medical record data and a process for storing text data additionally described in the medical record, etc., in the medical information database 50A. After a process for recording data in the medical information database 50A is finished, the electronic medical record application 30A is unable to write data to the medical information database 50A.

FIG. 2 is an exemplary block diagram showing a configuration of the wearable vital sensor 10.

As shown in FIG. 2, the wearable vital sensor includes, as vital sensors, for example, an electrocardiographic (ECG) sensor 201, a body temperature sensor 202, an acceleration sensor 203 and a pulse wave sensor 204.

The ECG sensor 201 includes a pair of electrodes. The ECG sensor 201 measures the potential difference between the electrodes. The body temperature sensor 202 measures the body temperature of the wearer. The acceleration sensor 203 measures the acceleration. The pulse wave sensor 204 includes a light-emitting diode (LED) and a photodiode (PD). The pulse wave sensor 204 detects the pulse wave by detecting the strength of light emitted from the LED and reflected from the human body.

The wearable vital sensor 10 further includes, for example, an analogue front end (AFE) 301, a feature amount extraction module 302, a wear determination module 303, a wearer authentication module 304 and a medical worker authentication module 305. The analogue front end 301 samples the potential difference of the pair of the electrocardiographic electrode of the ECG sensor 201. By this process, the analogue front end 301 generates an output time-series signal corresponding to a detection signal of the ECG sensor 201. The analogue front end 301 samples an output signal of the pulse wave sensor 204. By this process, the analogue front end 301 generates an output time-series signal corresponding to a detection signal of the pulse wave sensor 204. The analogue front end 301 includes, for example, an analogue/digital converter (ADC) 311, an amplifier (AMP) 312 and an automatic gain controller (AGC) 313.

[Feature Amount Extraction]

The feature amount extraction module 302 functions as a measurement module configured to measure a value related to a vital signal of a human body by analyzing at least one of an output time-series signal of the ECG sensor 201 and an output time-series signal of the pulse wave sensor 204 obtained by the analogue front end 301. The feature amount extraction module 302 includes an electrocardiographic measurement module 321, a heart rate/pulse rate measurement module 322, an R-R interval measurement module 323, a stress level measurement module 324 and a blood pressure measurement module 325.

The electrocardiographic measurement module 321 measures the electrocardiogram by analyzing output time-series signals of the ECG sensor 201. The heart rate/pulse rate measurement module 322 executes a process for measuring the heart rate based on the electrocardiogram obtained by the electrocardiographic measurement module 321 or a process for measuring the pulse rate by analyzing output time-series signals of the pulse wave sensor 204. The R-R interval measurement module 323 measures the R-R interval (RRI) which is the interval between two R-waves corresponding to two continuous heartbeats, respectively, based on the electrocardiogram obtained by the electrocardiographic measurement module 321.

The stress level measurement module 324 generates the above pulse interval data showing changes in the pulse intervals by analyzing output time-series signals of the pulse wave sensor 204. The stress level measurement module 324 measures the stress level based on the power spectrum of a low-frequency (LF) region and the power spectrum of a high-frequency (HF) region each of which is obtained by converting the pulse interval data for a predetermined period into a frequency spectrum distribution. In this case, LF/HF shows the stress level.

The blood pressure measurement module 325 measures the pulse wave transmission time (PWTT) based on the electrocardiogram and the pulse wave. The blood pressure measurement module 325 measures the blood pressure based on the PWTT and the initial value or based on the PWTT and the standard data.

While the vital sensor (the ECG sensor 201, the body temperature sensor 202, the acceleration sensor 203 and the pulse wave sensor 204) detects vital signals, the wear determination module 303 determines whether or not the user (a person) is wearing the vital sensor.

The measurement performed by each measurement module of the feature amount extraction module 302 may be repeatedly executed at regular intervals.

A controller 401 uses a wireless communication module 402 to transmit, to the daily vital-sign cloud server 40, the ID indicating the individual authenticated (specified) by the wearer authentication module 304 described later, and plural measurement results obtained by repeatedly performing measurement processes at regular intervals. The daily vital-sign cloud server 40 stores the data in the daily vital-sign database 40A corresponding to the ID (individual). The daily vital-sign cloud server 40 may calculate, for example, weekly or monthly average values or weekly or monthly moving average values by statistically processing a large number of measurement values accumulated in the daily vital-sign database 40A. The daily vital-sign cloud server 40 may calculate the change in annual average values year by year.

The wearable vital sensor 10 includes a near-field communication module 403. The near-field communication module 403 performs near-field communication with the near-field communication terminal 20. For the near-field communication, for example, the FeliCa (registered trademark), the ISO/IEC 14443 (MIFARE [registered trademark]), the ISO/IEC 18092 or the ISO/IEC 2148 is used.

The wearable vital sensor 10 includes an indicator 404. The indicator 404 is configured to function as a state display module for notifying the user that the measurement of vital signals is in progress. The indicator 404 may be one or more LEDs.

[Wear Determination]

The wear determination module 303 determines whether or not the wearable vital sensor is being worn by a person based on the impedance or noise level of various sensors.

The wear determination module 303 is configured to perform determination (contact determination) regarding whether or not a human body (skin) contacts the ECG sensor 201 by analyzing the frequency characteristics of time-series signals of the ECG sensor 201.

More specifically, the wear determination module 303 is configured to perform contact determination and stabilization determination related to the ECG sensor 201 as follows.

Here, it is assumed that the sampling frequency of output time-series signals of the ECG sensor 201 is 1000 Hz.

<Contact Determination for ECG Sensor>

The wear determination module 303 determines that a time-series signal portion of the ECG sensor 201 which does not include the frequency component of a first frequency band (in short, a frequency component with 3 to 45 Hz) is a time-series signal portion corresponding to a period in a contactless state in which the user does not contact the ECG sensor 201. The contact determination may be performed by measuring the impedance of the electrocardiographic electrode with hardware. The contact determination may be performed with a proximity sensor.

The wear determination module 303 is configured to perform contact determination related to the pulse wave sensor 204 as follows.

Here, it is assumed that the sampling frequency of output time-series signals of the pulse wave sensor 204 is 125 Hz.

<Contact Determination for Pulse Wave Sensor>

The wear determination module 303 determines that a time-series signal portion of the pulse wave sensor 204 which does not include the frequency component of a second frequency band (in short, a frequency component with 5 to 50 Hz) is a time-series signal portion corresponding to a period in a contactless state in which the user does not contact the pulse wave sensor 204. The contact determination may be performed with a proximity sensor.

FIG. 3 is shown for explaining an operation for calculating the stress level (stress index).

(1) Calculation of Pulse Interval from Pulse Wave

The feature amount extraction module 302 removes a time-series signal portion corresponding to a period in a contactless state and a time-series signal portion corresponding to a period in an unstable state from the output time-series signal of the pulse wave sensor 204 and obtains the time-series signal (pulse wave signal) which is used to analyze the pulse interval. In other words, the feature amount extraction module 302 connects time-series signal portions of the output time-series signal excluding the time-series signal portion corresponding to a period in a contactless state and the time-series signal portion corresponding to a period in an unstable state. In short, the feature amount extraction module 302 connects time-series signal portions each corresponding to a period in a stable state. In this manner, the feature amount extraction module 302 obtains a time-series signal (pulse wave signal) which is used to analyze the pulse interval.

The feature amount extraction module 302 detects the peak position of each pulsation from the obtained pulse wave signal and calculates, for each detected peak position, the pulse interval indicating the time distance (pulse interval) between the detected peak position and the peak position immediately before the detected peak position. Thus, it is possible to obtain time-series pulse interval data showing changes in the pulse interval.

(2) Interpolation of Pulse Interval into Equal Time Interval Data

The feature amount extraction module 302 interpolates time-series pulse interval data and converts it into equal time interval data (in short, re-sampling). The square marks in the upper right graph in FIG. 3 show the original pulse interval data. The circular marks in the upper right graph in FIG. 3 show the pulse interval data obtained by interpolation.

(3) Frequency Analysis of Fluctuation in Pulse Interval

The feature amount extraction module 302 analyses the frequency of equal time interval data and calculates the power spectrum of a low-frequency (LF) region and the power spectrum of a high-frequency (HF) region. The power spectrum of a low-frequency (LF) region is a value which reflects the sympathetic nerve activity. The power spectrum of a high-frequency (HF) region is a value which reflects the parasympathetic nerve activity.

(4) Stress Level

The feature amount extraction module 302 calculates the activity of the sympathetic nerve (LF/HF).

[Wearer Authentication]

When the wear determination module 303 determines that the vital sensor is being worn by a person, the wearer authentication module 304 determines the wearer based on the feature amount calculated by the feature amount extraction module 302. For example, the wearer authentication module 304 has authentication data for specifying the user for each user of the wearable vital sensor. The authentication data is calculated based on, for example, the blood pressure measured in the past. The blood pressure differs depending on the age, etc., and differs depending on the measurement time. Thus, the wearer can be authenticated (specified) based on the time and the blood pressure.

[Medical Worker Authentication]

When the wearable vital sensor 10 is placed on the near-field communication terminal 20, and the computer 30 accesses the wearable vital sensor 10 via the near-field communication terminal 20, the medical worker authentication module 305 determines whether or not a write access right may be given to the computer 30 by authenticating whether or not the operator of the computer 30 is a medical worker. A medical worker ID and a medical worker authentication password are given to a medical worker. The medical worker authentication password is generated by inputting the medical worker ID into predetermined algorithm. After the medical worker ID and the medical worker authentication password are generated from the computer 30, the medical worker authentication module 305 generates a character string by inputting the medical worker ID into the algorithm used for the generation of the medical worker authentication password. When the medical worker authentication password transmitted from the computer 30 agrees with the generated character string, the medical worker authentication module 305 determines that the operator is a medical worker. When the medical worker authentication module 305 determines that the operator is a medical worker, and a write access right may be given to the computer 30, the medical worker authentication module 305 notifies the controller 401 of the user ID showing the person who is authenticated before the placement on the near-field communication terminal 20 and the write access password for write access to the medical information database 50A. The controller 401 performs a process for transmitting the user ID and the write access password to the electronic medical record application 30A through the near-field communication module.

The write access password may be a one-time password. For example, the one-time password is generated from the password which was lastly informed to the computer 30. Transmission of the ID and the one-time password to the daily vital-sign cloud server 40 and the medical information cloud server 50 enables access to the daily vital-sign database 40A and the medical information database 50A. The medical information cloud server 50 generates a password, using the same algorithm as the algorithm used by the medical worker authentication module 305 for the generation of the one-time password.

By using the one-time password, it is possible to prevent the medical worker from writing data to the medical information database 50A after the medical worker finishes writing data to the medical information database.

[State Transition of Wearable Vital Sensor]

Figure 4:
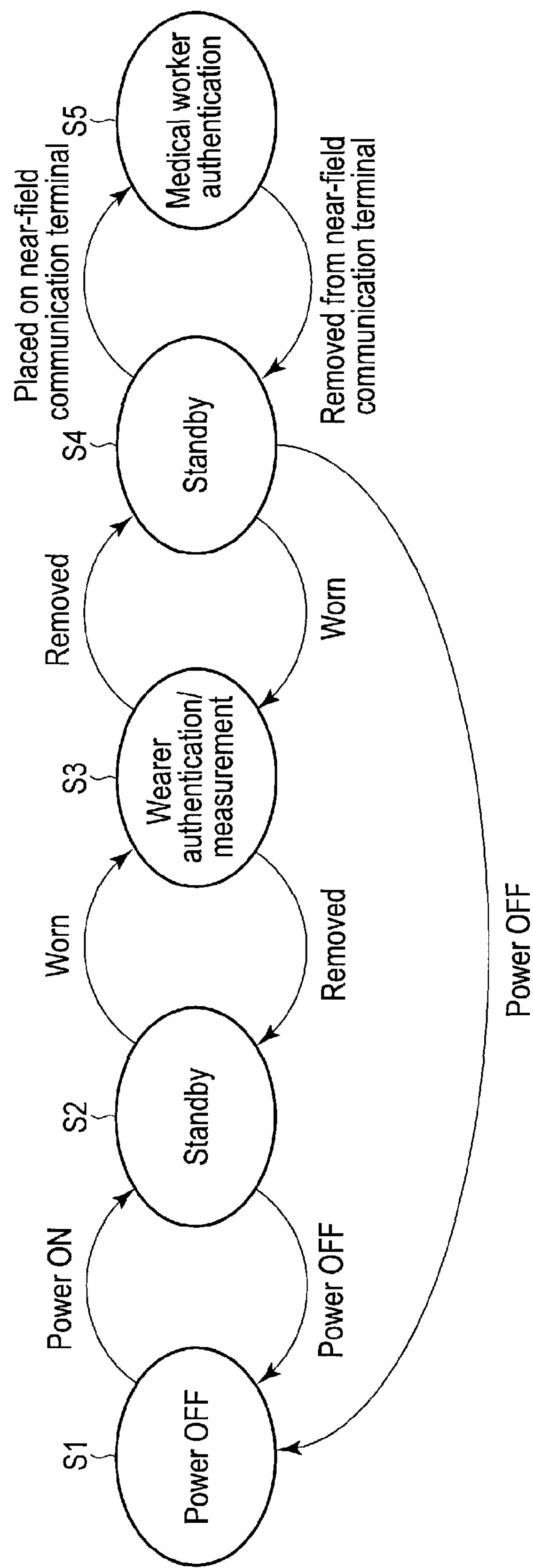
FIG. 4 exemplarily shows the state transition of a wearable vital sensor.

The state transition of the wearable vital sensor is explained with reference to FIG. 4.

When the wearable vital sensor 10 is turned on from a power-off state (S1), the wearable vital sensor 10 transitions to a standby state (S2). When the wearable vital sensor 10 is worn by a person, the wearable vital sensor 10 performs wearer authentication and measurement of vital signs (S3). When the wearable vital sensor 10 is removed from the person, the wearable vital sensor 10 transitions to a standby state (S4).

The wearable vital sensor 10 performs medical worker authentication (S5) when the wearable vital sensor 10 is placed on the near-field communication terminal 20 in a standby state (S4). When the wearable vital sensor 10 transitions to a non-placement state in which the wearable vital sensor 10 is not on the near-field communication terminal 20, the wearable vital sensor 10 transitions to a standby state (S4). When the wearable vital sensor 10 is turned off in a standby state (S2 or S4), the wearable vital sensor 10 transitions to a power-off state (S1).

[State Transition of Medical Information Database]

The state transition of the medical information database 50A when the medical worker authentication is successful will be explained, referring to FIG. 5.

In a normal state, data cannot be written to the medical information database 50A (S11). When the computer 30 receives an ID and a password from the wearable vital sensor 10, and the ID and the password are transmitted from the computer 30 to the medical information cloud server 50, and the authentication is successful, the state is changed to a state in which data can be written to the medical information database 50A (S12). After the writing is finished, the state returns to a state in which data cannot be written to the medical information database 50A (S11).

[Status of Use in Medical Institutions]

Figure 6:
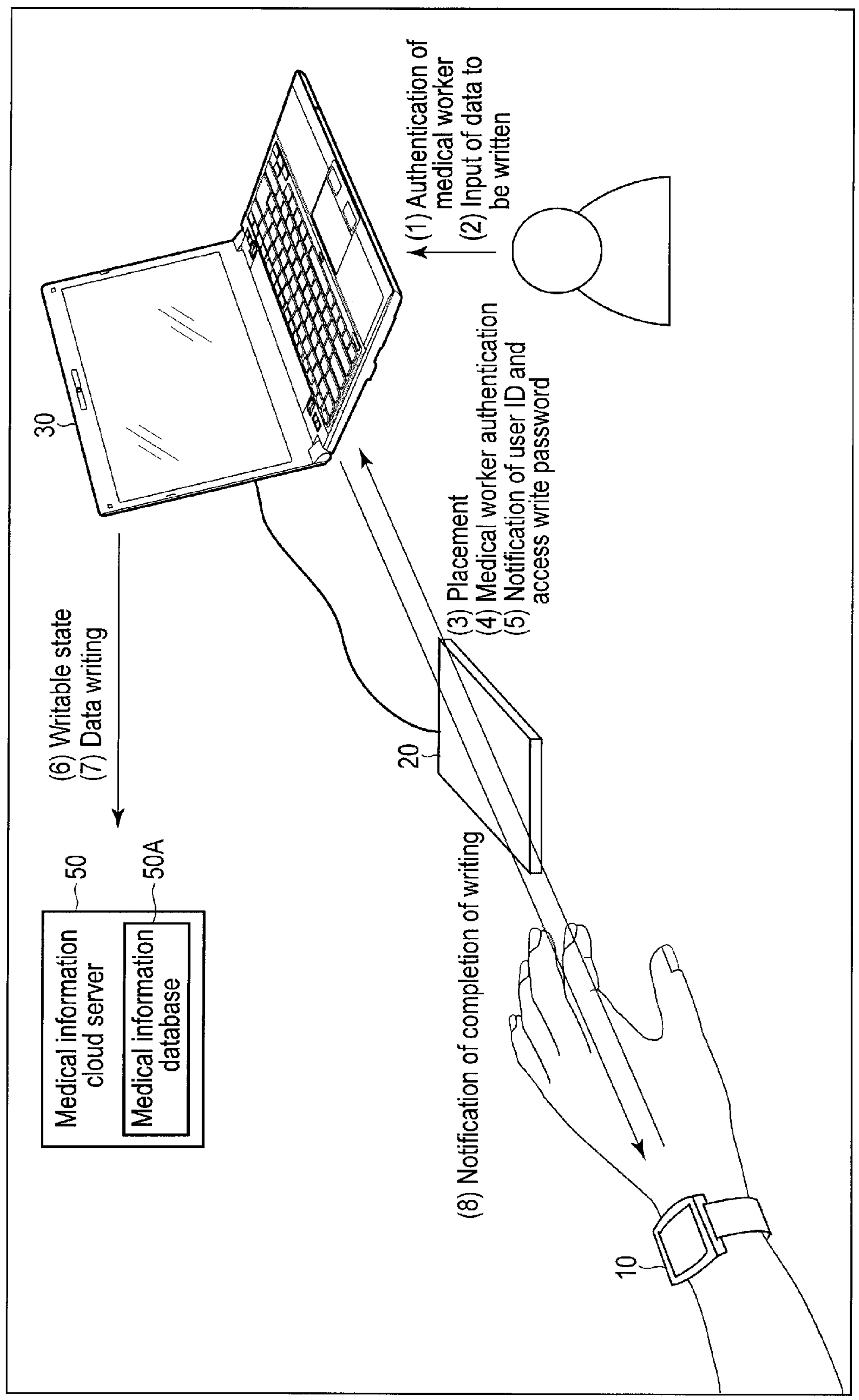
FIG. 6 exemplarily shows the status of use of the wearable vital sensor, a computer, an electronic medical record application, a medical information cloud server and the medical information database in a medical institution.

This specification explains the status of use of the wearable vital sensor 10, the computer 30, the electronic medical record application 30A, the medical information cloud server 50 and the medical information database 50A in a medical institution with reference to FIG. 6.

(1) Authentication of Medical Worker

First, a medical worker inputs a medical worker ID and a read access password in the electronic medical record application 30A. The electronic medical record application 30A transmits the input medical worker ID and read access password to the medical information cloud server 50. The medical information cloud server 50 performs medical worker authentication based on the received medical worker ID and read access password. When the medical worker authentication is successful, the electronic medical record application 30A is allowed to read data from the medical information database 50A.

(2) Input

The electronic medical record application 30A displays, for example, a medical record on the display screen of the computer 30 based on the data read from the medical information database 50A. The medical worker inputs, in the electronic medical record application 30A, data to be stored in the medical information database 50A.

(3) Placement

The wearer removes the wearable vital sensor 10. The wearable vital sensor 10 is placed on the near-field communication terminal 20.

(4) Medical Worker Authentication

The electronic medical record application 30A transmits the medical worker ID and a medical worker authentication password to the wearable vital sensor 10 through the near-field communication terminal 20. The wearable vital sensor 10 performs medical worker authentication, using the medical worker ID and the medical worker authentication password.

(5) Transmission of User ID and Write Access Password

When the medical worker authentication is successful, the wearable vital sensor 10 transmits a user ID and a write access password to the electronic medical record application 30A.

(6) Permission of Writing to Medical Information Database

The electronic medical record application 30A transmits the user ID and the write access password to the medical information cloud server 50. When the authentication using the user ID and the write access password is successful in the medical information cloud server 50, data can be written to the medical information database 50A. The medical information cloud server 50 informs that data can be written to the medical information database 50A.

(7) Data Writing

The electronic medical record application 30A transmits data to be written to the medical information database 50A. The medical information cloud server 50 writes data to the medical information database 50A based on the received data.

(8) Notification of Completion of Writing

The electronic medical record application 30A notifies the wearable vital sensor 10 that the writing is finished.

As described above, in the present embodiment, the wearable vital sensor 10 notifies the electronic medical record application 30A of a user ID and a write access password for providing a write access right to the medical information database 50A corresponding to the user. In this manner, a medical institution is prevented from writing data to the medical information database 50A corresponding to the user when the user is not present in the medical institution.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. A wearable electronic device comprising:

a communication circuitry configured to communicate with an external device, the external device able to access a server; and a processor configured to receive identification information and a password of a first user of the external device from the external device by means of the communication circuitry, authenticate the first user of the external device based on the identification information and the password received from the external device, and transmit access right information to the external device by means of the communication circuitry when the first user of the external device is authenticated, the access right information indicative of a write access right to first data stored in the server, the first data relating to a second user of the wearable electronic device.

2. The wearable electronic device of claim 1, further comprising a vital sensor configured to measure a vital sign of the second user of the wearable electronic device.

3. The wearable electronic device of claim 2, wherein the processor is further configured to transmit second data comprising the vital sign to the server.

4. The wearable electronic device of claim 2, wherein the vital sensor comprises at least one of an electrocardiographic sensor, a body temperature sensor, an acceleration sensor and a pulse wave sensor.

5. The wearable electronic device of claim 2, wherein the processor is further configured to determine whether the wearable electronic device is worn based on the vital sign.

6. The wearable electronic device of claim 2, wherein the processor is further configured to identify the second user of the wearable electronic device based on the vital sign.

7. The wearable electronic device of claim 1, wherein the communication circuitry comprises a near-field communication circuitry.

8. The wearable electronic device of claim 1, wherein the access right information is indicative of a write access right to medical information stored in the server and related to the second user of the wearable electronic device, the medical information comprising an inspection result, a diagnosis, or a prescription drug.

9. A method for a wearable electronic device, the method comprising:

connecting the wearable electronic device to an external device, the external device able to access a server;

receiving identification information and a password of a first user of the external device from the external device, authenticating the first user of the external device based on the identification information and the password received from the external device, and transmitting access right information to the external device when the first user of the external device is authenticated, wherein the access right information is indicative of a write access right to first data stored in the server, the first data relating to a second user of the wearable electronic device.

10. The method of claim 9, further comprising measuring a vital sign of the second user of the wearable electronic device.

11. The method of claim 10, further comprising transmitting second data comprising the vital sign to the server.

12. The method of claim 10, wherein the vital sign is measured by means of a vital sensor comprising at least one of an electrocardiographic sensor, a body temperature sensor, an acceleration sensor and a pulse wave sensor.

13. The method of claim 10, further comprising determining whether the electronic device is worn based on the vital sign.

14. The method of claim 10, further comprising identifying the second user of the wearable electronic device based on the vital sign.

15. The method of claim 9, wherein the connecting comprises connecting the wearable electronic device to the external device by means of a near-field communication circuitry.

16. The method of claim 9, wherein the access right information is indicative of a write access right to medical information stored in the server and related to the second user of the wearable electronic device, the medical information comprising an inspection result, a diagnosis, or a prescription drug.

17. A non-transitory computer-readable storage medium storing a computer program executable by a computer of a wearable electronic device, the computer program controlling the computer to execute functions of:

connecting the wearable electronic device to an external device, the external device able to access a server;

receiving identification information and a password of a first user of the external device from the external device, authenticating the first user of the external device based on the identification information and the password received from the external device, and transmitting access right information to the external device when the first user of the external device is authenticated, wherein the access right information is indicative of a write access right to first data stored in the server, the first data relating to a second user of the wearable electronic device.

* * * * *